United States Patent
Baek et al.

(10) Patent No.: US 10,722,548 B2
(45) Date of Patent: Jul. 28, 2020

(54) METHOD OF PREPARING LYOPHILIZATE OF TAHEEBO ALCOHOL EXTRACT

(71) Applicants: NUTRIBIOTECH, Seoul (KR); NUTRISCIENCE CO., LTD., Seoul (KR)

(72) Inventors: Kwang Soo Baek, Seoul (KR); Jin Hak Kim, Seoul (KR); Su Young Choi, Seoul (KR); Young Min Park, Goyang-si (KR); Jae Seok Shim, Seongnam-si (KR); Sang Woo Kim, Seongnam-si (KR); Mann Seok Yoon, Yongin-si (KR); Yoon Jong Lee, Seoul (KR)

(73) Assignees: COSMAX NBT, INC., Seoul (KR); COSMAX NS, INC., Seoul (KR)

(*) Notice: Subject to any disclaimer, the term of this patent is extended or adjusted under 35 U.S.C. 154(b) by 0 days.

(21) Appl. No.: 16/313,270

(22) PCT Filed: Jul. 14, 2017

(86) PCT No.: PCT/KR2017/007605
§ 371 (c)(1),
(2) Date: Dec. 26, 2018

(87) PCT Pub. No.: WO2019/013374
PCT Pub. Date: Jan. 17, 2019

(65) Prior Publication Data
US 2019/0167746 A1    Jun. 6, 2019

(51) Int. Cl.
| | |
|---|---|
| *A61K 36/185* | (2006.01) |
| *A61K 36/53* | (2006.01) |
| *A23L 33/105* | (2016.01) |
| *A61K 8/9783* | (2017.01) |
| *A61Q 19/00* | (2006.01) |
| *A61K 9/19* | (2006.01) |
| *A61K 47/46* | (2006.01) |
| *A61K 8/9789* | (2017.01) |
| *A61K 9/00* | (2006.01) |
| *A61Q 17/00* | (2006.01) |

(52) U.S. Cl.
CPC ............ *A61K 36/53* (2013.01); *A23L 33/105* (2016.08); *A61K 8/9783* (2017.08); *A61K 8/9789* (2017.08); *A61K 9/0014* (2013.01); *A61K 9/19* (2013.01); *A61K 36/185* (2013.01); *A61K 47/46* (2013.01); *A61Q 19/00* (2013.01); *A61K 2236/00* (2013.01); *A61Q 17/005* (2013.01)

(58) Field of Classification Search
None
See application file for complete search history.

(56) References Cited

U.S. PATENT DOCUMENTS

| | | | | | |
|---|---|---|---|---|---|
| 5,663,197 | A | * | 9/1997 | Ueda | C07D 307/92 514/468 |
| 6,245,807 | B1 | * | 6/2001 | Pardee | A61K 31/352 514/454 |
| 2005/0002962 | A1 | * | 1/2005 | Pasco | A61K 36/07 424/195.15 |
| 2006/0142271 | A1 | * | 6/2006 | Muller | C07D 307/92 514/220 |
| 2014/0154319 | A1 | * | 6/2014 | Kwak | A61K 31/352 424/484 |

FOREIGN PATENT DOCUMENTS

| | | |
|---|---|---|
| KR | 10-2007-0113465 A | 11/2007 |
| KR | 10-2007-0090392 * | 3/2009 |
| KR | 10-2009-0025497 A | 3/2009 |
| KR | 10-2010-0009136 A | 1/2010 |
| KR | 10-2013-0128887 A | 11/2013 |
| KR | 10-2014-0029561 A | 3/2014 |

OTHER PUBLICATIONS

Freitas A. et al. Antidepressant Like Action of the Bark Ethanolic Extract from Tabebuia avellanedae . . . J of Ethnopharmacology 145 (3)737-745, 2013. (Year: 2013).*

Choi W. et al. Ethanolic Extract of Taheebo Attenuates Increase in Body Weight and Fatty Liver in Mice Fed a High Fat Diet. Molecules 19:16013-23, 2014. (Year: 2014).*

Park J. et al. Tabetri Ameliorates Atopic Dermatitis Symptoms in Mice Mediators of Inflammation 2018:1-11, 2018 (Year: 2018).*

Mukherjee B. et al. Growth Inhibition of Estrogen Receptor Positive Human Breast Cancer Cells by Taheebo . . . Int J of Molecular Medicine 24:253-260, 2009. (Year: 2009).*

* cited by examiner

*Primary Examiner* — Ralph J Gitomer

(74) *Attorney, Agent, or Firm* — Don D. Cha; HDC IP Law, LLP

(57) ABSTRACT

The present invention relates to a method of preparing a lyophilizate of a Taheebo alcohol extract, including: (a) extracting Taheebo with an alcohol and concentrating an extract; and (b) lyophilizing the alcohol-extracted and concentrated Taheebo, and a composition for the treatment, prevention or amelioration of an inflammatory disease including a lyophilizate of a Taheebo alcohol extract prepared therefrom.

4 Claims, 1 Drawing Sheet

METHOD OF PREPARING LYOPHILIZATE OF TAHEEBO ALCOHOL EXTRACT

CROSS-REFERENCE TO RELATED APPLICATIONS

This is a U.S. National Stage Application under 35 U.S.C. § 371 of PCT Patent Application No. PCT/KR2017/007605, filed Jul. 14, 2017, which is incorporated herein by reference in its entirety.

TECHNICAL FIELD

The present invention relates to a method of preparing a lyophilizate of a Taheebo alcohol extract.

BACKGROUND ART

Taheebo is the common name for Tabebuia avellanedae of the family Bignoniaceae, which is a big tree with a diameter of 2 to 3 meters and a height of 30 m. This tree of about 100 species is often used for landscaping in South American cities, and is also popular for its wood. The tree has excellent quality and has the best durability among tropical trees.

In Taheebo, which is a tree with purple blooms and only native to the Amazon region, only an inner bark with about 7 mm in thickness between an outer shell and lignin of is only used as a medicinal material. Many other species of trees have pink, yellow or white flowers, and these species have phytochemicals (chemical component of plant) and have a small amount of various active ingredients or have no active ingredients.

Further, Taheebo was found to be efficacious in anticancer treatments as well as in a wide range of antibiotic, antiviral, antibacterial and antihepatitis treatments in clinical trials thereof, and has been widely used for diabetes, hypertension, and atopy treatments in developed countries. However, it was confirmed that no studies have been conducted on a method of preparing Taheebo to improve the efficacy against inflammatory diseases of Taheebo.

DISCLOSURE

Technical Problem

The present invention provides a method of preparing a lyophilizate of a Taheebo alcohol extract, including: (a) extracting Taheebo with an alcohol and concentrating an extract; and (b) lyophilizing the alcohol-extracted and concentrated Taheebo, and the like.

However, the scope of the present invention is not limited to the above-described object, and other unmentioned objects may be clearly understood by those skilled in the art from the following description.

Technical Solution

The present invention provides a method of preparing a lyophilizate of a Taheebo alcohol extract, including: (a) extracting Taheebo with an alcohol and concentrating an extract; and (b) lyophilizing the alcohol-extracted and concentrated Taheebo.

In Step (a), a concentration of ethanol in the alcohol may be in a range of 50 to 90 (v/v)%.

In Step (a), the extracting may be performed at a temperature of 40 to 80° C. for 3 to 10 hours.

In Step (a), the lyophilizing is performed at a temperature of −30 to −50° C. for 48 to 168 hours.

The lyophilizate of a Taheebo alcohol extract may have an inhibitory effect of nitric oxide synthesis.

According to an embodiment of the present invention, there is provided a pharmaceutical composition for the prevention or treatment of an inflammatory disease, including a lyophilizate of a Taheebo alcohol extract prepared using the above-described method.

The inflammatory disease may be one or more selected from the group consisting of allergies, dermatitis, atopy, conjunctivitis, periodontitis, rhinitis, otitis media, laryngopharyngitis, tonsillitis, pneumonia, gastric ulcers, gastritis, Crohn's disease, colitis, gout, ankylosing spondylitis, rheumatic fever, lupus, fibromyalgia, psoriatic arthritis, osteoarthritis, rheumatoid arthritis, periarthritis, tendonitis, tenosynovitis, peritendinitis, myositis, hepatitis, cystitis, nephritis, Sjogren's syndrome, multiple sclerosis, and acute and chronic inflammatory diseases.

According to another embodiment of the present invention, there is provided a dietary supplement for the prevention or amelioration of an inflammatory disease, including a lyophilizate of a Taheebo alcohol extract prepared using the above-described method.

According to still another embodiment of the present invention, there is provided a skin preparation for external use for the prevention or treatment of an inflammatory disease, including a lyophilizate of a Taheebo alcohol extract prepared using the above-described method.

According to yet another embodiment of the present invention, there is provided a cosmetic composition for prevention or amelioration of an inflammatory disease, including a lyophilizate of a Taheebo alcohol extract prepared using the above-described method.

Advantageous Effects

In the method of preparing a lyophilizate of a 50 to 90 (v/v)% alcohol extract of Taheebo according to the present invention, a lyophilization method is used in a drying process while a 50 to 90 (v/v)% alcohol is used as a solvent in an extraction process. As a result, the inhibitory effect of nitric oxide synthesis can be greatly improved, the lyophilizate can be variously used as a composition for the prevention, amelioration or treatment of an inflammatory disease.

BEST MODE OF THE INVENTION

Figure 1:
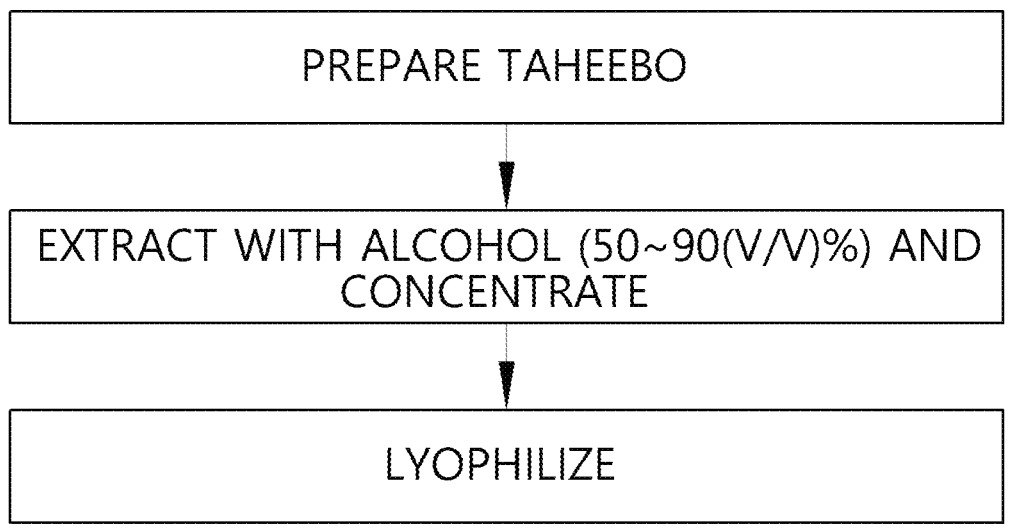
FIG. 1 is a schematic view showing a method for preparing a lyophilizate of a 50 to 90 (v/v)% alcohol extract of Taheebo according to an embodiment of the present invention.

The inventors of the present invention found that, in a method of preparing dry Taheebo extract matter, when a lyophilization method is used in a drying process while a 50 to 90 (v/v)% alcohol is used as a solvent in an extraction process, the inhibitory effect of nitric oxide synthesis can be greatly improved, thereby completing the present invention.

Hereinafter, the present invention will be described in detail.

Method of Preparing Lyophilizate of Taheebo Alcohol Extract

The present invention provides a method of preparing a lyophilizate of a Taheebo alcohol extract, including: (a) extracting Taheebo with an alcohol and concentrating an extract; and (b) lyophilizing the alcohol-extracted and concentrated Taheebo.

First, the method of preparing a lyophilizate of a Taheebo alcohol extract according to the present invention includes a step [Step (a)] of extracting Taheebo with an alcohol and concentrating an extract.

In the present specification, the term "Taheebo" refers to Tabebuia avellanedae of family Bignoniaceae. In the present invention, Brazilian Taheebo was used. Specifically, the bark (inner and outer bark), leaves, flowers, stems and roots of Taheebo may be a target for extraction, but it is preferable to extract the bark inside Taheebo, that is, the inner bark of Taheebo, and the present invention is not limited thereto.

The extraction is characterized by being carried out using an alcohol as a solvent. The concentration of ethanol in the alcohol is preferably in the range of 50 to 90 (v/v)%, and the concentration of ethanol in the alcohol is more preferably in the range of 70 to 90 (v/v)%, but the present invention is not limited thereto. When the concentration of the ethanol in the alcohol is too low, it is confirmed that the inhibitory effect of nitric oxide synthesis is insignificant. When the concentration of the ethanol in the alcohol is too high, productivity decreases due to a decrease in yield and difficulty in industrial application.

That is, in when the extraction is performed using hot water as a solvent instead of extracting with the alcohol as a solvent as described above, the degree of improving the inhibitory effect of nitric oxide synthesis is insignificant.

Further, the extraction may be carried out at a temperature of 40 to 80° C. for 3 to 10 hours.

Specifically, the extraction is preferably performed by adding the alcohol at 2 to 20 times the weight of the Taheebo (specifically, 50 to 90 (v/v)% alcohol) to Taheebo, and more preferably, performed by adding the alcohol at 5 to 15 times the weight of the Taheebo, but the present invention is not limited thereto. The extraction temperature is preferably in the range of 40 to 80° C., more preferably in the range of 50 to 60° C., but the present invention is not limited thereto. The extraction time is preferably in the range of 3 to 6 hours, but the present invention is not limited thereto. The extraction method may be a cold extraction method, an ultrasonic extraction method or a reflux extraction method, but the present invention is not limited thereto. The number of times of extraction is preferably in the range of 1 to 5 times, and it is more preferable to repeat the extraction 2 to 3 times, but the present invention is not limited thereto. In addition, the Taheebo alcohol extract may be concentrated.

Next, the method of preparing a lyophilizate of a Taheebo alcohol extract according to the present invention includes a step [Step (b)] of lyophilizing the alcohol-extracted and concentrated Taheebo.

In the present specification, the term "lyophilizaion" is also referred to as freeze-drying, which is a method of rapidly lowering the temperature of the container and freezing the Taheebo alcohol extract to be dried, setting the pressure inside the container to be close to vacuum so that the solidified solvent contained in the Taheebo alcohol extract is immediately sublimed into vapor and dried.

The lyophilization may be performed at a temperature of −30 to −50° C. for 48 to 168 hours. In the case of the lyophilization, as compared to conventional spray-drying, the inhibitory effect of nitric oxide synthesis can be greatly improved.

The lyophilizate of a Taheebo alcohol extract prepared by the above-described method contains veratric acid as an indicator component, and the content of the veratric acid in the lyophilizate of a Taheebo alcohol extract is preferably in the range of about 1.0 to 5.0 (w/w)%, and more preferably, about 1.0 to 3.0 (w/w)%, but the present invention is not limited thereto.

Therefore, the method of preparing the lyophilizate of a 50 to 90 (v/v)% alcohol extract of Taheebo according to the present invention is characterized in that a 50 to 90 (v/v)% alcohol is used as a solvent in the extraction process while a lyophilizaion method is used in the drying process, significantly improving the inhibitory effect of nitric oxide synthesis. Accordingly, the method can be variously used as a composition for the prevention, amelioration or treatment of an inflammatory disease.

Composition for Prevention, Amelioration or Treatment of Inflammatory Disease

According to an embodiment of the present invention, there is provided a pharmaceutical composition for the prevention or treatment of an inflammatory disease, including a lyophilizate of a Taheebo alcohol extract which is prepared by (a) extracting Taheebo with an alcohol and concentrating an extract; and (b) lyophilizing the alcohol-extracted and concentrated Taheebo.

The lyophilizate of a Taheebo alcohol extract and the extraction process and drying process for preparing the lyophilizate are as described above.

Further, the inflammatory disease may be one or more selected from the group consisting of allergies, dermatitis, atopy, conjunctivitis, periodontitis, rhinitis, otitis media, laryngopharyngitis, tonsillitis, pneumonia, gastric ulcers, gastritis, Crohn's disease, colitis, gout, ankylosing spondylitis, rheumatic fever, lupus, fibromyalgia, psoriatic arthritis, osteoarthritis, rheumatoid arthritis, periarthritis, tendonitis, tenosynovitis, peritendinitis, myositis, hepatitis, cystitis, nephritis, Sjogren's syndrome, multiple sclerosis, and acute and chronic inflammatory diseases.

Specifically, the pharmaceutical composition may be prepared in a form including oral dosage form such as a powder, granule, tablet, capsule, suspension, emulsion, syrup, aerosol and the like, and a form of an external preparation, suppository and sterile injection, and may additionally include a suitable carrier, adjuvant or diluent commonly used in the preparation of the pharmaceutical composition for formulation.

Examples of the carrier, adjuvant or diluent include various compounds or mixtures including lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil, etc.

In the case of formulation, the formulation may be prepared using diluents or adjuvants such as fillers, weighing agents, binders, humectants, disintegrants, surfactants and the like which are usually used.

The solid preparations for oral administration may be prepared by mixing at least one adjuvant such as starch, calcium carbonate, sucrose or lactose, gelatin and the like with the lyophilizate of a Taheebo alcohol extract. Further, lubricants such as magnesium stearate and talc may also be used in addition to simple adjuvants.

Examples of liquid preparations for oral administration include suspensions, internal use solutions, emulsions, syrups, etc. In addition to a simple diluent such as water or liquid paraffin, various excipients such as wetting agents, sweetening agents, aromatics, preservatives, and the like may be contained in the liquid preparations.

Examples of preparations for administration via a non-oral route include sterile aqueous solutions, non-aqueous solvents, suspensions, emulsions, lyophilizates and suppositories. Propylene glycol, polyethylene glycol, vegetable oils such as olive oil, injectable esters such as ethyl oleate and the like may be used as non-aqueous solvents and suspensions. The basic materials of suppositories include Witepsol, macrogol, Tween 61, cacao butter, laurin butter, glycerol, gelatin, etc.

The desirable dose of the pharmaceutical composition varies depending on the condition and the weight of the patient, severity of a disease, drug form, route and period of administration, and may be suitably chosen by those skilled in the art. However, in order to obtain desirable effects, the pharmaceutical composition may be administered at the amount in the range of 0.0001 to 2,000 mg/kg, preferably, 0.001 to 2,000 mg/kg per day. The dose may be administered in a single or multiple doses per day. However, the scope of the present invention is not limited by the dose.

The pharmaceutical composition may be administered to mammals such as rats, mice, livestock or humans via various routes. All modes of administration are contemplated, for example, administration may be performed orally, intrarectally or by intravenous, intramuscular, subcutaneous, intrauterine or intracerebroventricular injection.

According to another embodiment of the present invention, there is provided a dietary supplement for the prevention or amelioration of an inflammatory disease, including a lyophilizate of a Taheebo alcohol extract which is prepared by (a) extracting Taheebo with an alcohol and concentrating an extract; and (b) lyophilizing the alcohol-extracted and concentrated Taheebo.

The lyophilizate of a Taheebo alcohol extract and the extraction process and drying process for preparing the lyophilizate are as described above.

Further, the inflammatory disease may be one or more selected from the group consisting of allergies, dermatitis, atopy, conjunctivitis, periodontitis, rhinitis, otitis media, laryngopharyngitis, tonsillitis, pneumonia, gastric ulcers, gastritis, Crohn's disease, colitis, gout, ankylosing spondylitis, rheumatic fever, lupus, fibromyalgia, psoriatic arthritis, osteoarthritis, rheumatoid arthritis, periarthritis, tendonitis, tenosynovitis, peritendinitis, myositis, hepatitis, cystitis, nephritis, Sjogren's syndrome, multiple sclerosis, and acute and chronic inflammatory diseases.

Specifically, in the dietary supplement, when the lyophilizate of a Taheebo alcohol extract is used as an additive for a dietary supplement, the lyophilizate may be used as it is, or may be used together with other foods or food ingredients, and may be suitably used according to a conventional method. The amount of the active ingredients to be mixed may be suitably determined according to each purpose of use such as prevention, health, treatment, etc.

The formulation of the dietary supplement may be in the form of powders, granules, pills, tablets, capsules, as well as in the form of general foods or beverages.

The type of the food is not particularly limited. Examples of foods to which the material may be added include meats, sausages, bread, chocolate, candies, snacks, confectioneries, pizza, ramen, other noodles, gum, dairy products including ice cream, various soups, beverages, teas, drinks, alcoholic beverages, multivitamin preparations or the like, and include all of typical foods.

Generally, in the preparation of foods or beverages, the lyophilizate of a Taheebo alcohol extract may be added in an amount of 15 parts by weight or less, preferably 10 parts by weight or less based on 100 parts by weight of a raw material. However, in the case of long-term ingestion intended for health or hygiene purposes or for the purpose of controlling health, the amount may be less than the above-described range. Further, the lyophilizate may be used in an amount of more than the above-described range since there is no problem in terms of safety because a natural substance is used in the present invention.

Among the dietary supplement, beverages may contain various flavoring agents or natural carbohydrates as additional components as in ordinary beverages. The above-described natural carbohydrates may be monosaccharides such as glucose and fructose, disaccharides such as maltose and sucrose, polysaccharides such as dextrin and cyclodextrin, and sugar alcohols such as xylitol, sorbitol, erythritol, etc. As a sweetening agent, natural sweetening agents such as thaumatin, stevia extract, synthetic sweetening agents such as saccharin and aspartame, and the like may be used. The content of the natural carbohydrate may be in the range of about 0.01 to 0.04 g, and preferably in the range of about 0.02 to 0.03 g per 100 mL of the beverage.

In addition, the dietary supplement may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, and carbonating agents used in carbonated beverages. In addition, the dietary supplement may contain flesh for the production of natural fruit juice, fruit juice drink and vegetable drink. The components may be used independently or in combination. The content of the additives is not limited, but is generally selected in the range of 0.01 to 0.1 parts by weight based on 100 parts by weight of the dietary supplement of the present invention.

According to another embodiment of the present invention, there is provided a skin preparation for external use for the prevention or treatment of an inflammatory disease, including a lyophilizate of a Taheebo alcohol extract prepared by (a) extracting Taheebo with an alcohol and concentrating an extract; and (b) lyophilizing the alcohol-extracted and concentrated Taheebo.

The lyophilizate of a Taheebo alcohol extract and the extraction process and drying process for preparing the lyophilizate are as described above.

Further, the inflammatory disease may be one or more selected from the group consisting of allergies, dermatitis, atopy, conjunctivitis, periodontitis, rhinitis, otitis media, laryngopharyngitis, tonsillitis, pneumonia, gastric ulcers, gastritis, Crohn's disease, colitis, gout, ankylosing spondylitis, rheumatic fever, lupus, fibromyalgia, psoriatic arthritis, osteoarthritis, rheumatoid arthritis, periarthritis, tendonitis, tenosynovitis, peritendinitis, myositis, hepatitis, cystitis, nephritis, Sjogren's syndrome, multiple sclerosis, and acute and chronic inflammatory diseases.

Specifically, examples of a suitable formulation used as the skin preparation for external use include solutions, gels, solid or paste preparations, oil-in-water emulsions, suspensions, microemulsions, microcapsules, microgranules or ionic liposomes, non-ionic vesicle dispersions, creams, skins, lotions, powders, ointments, sprays, etc. Further, it may be prepared into a foam form or an aerosol composition form further including a compressed propellant.

In addition to the lyophilizate of a Taheebo alcohol extract, the skin preparation for external use may additionally include lipids, organic solvents, dissolving agents, thickening agents, gelling agents, softeners, anti-oxidants, suspending agents, stabilizers, foaming agents, aromatics, surfactants, water, ionic or non-ionic emulsifiers, fillers, sequestering agents, chelating agents, preservatives, vitamins, UV blocking agents, wetting agents, essential oils, dyes, pigments, hydrophilic or lipophilic activators, liposomes, or other supplements commonly used in the field of dermatology such as any other ingredient commonly used in the skin preparation for external use. Further, the above-described ingredients may be introduced in amounts commonly used in the field of dermatology.

According to another embodiment of the present invention, there is provided a cosmetic composition for the prevention or amelioration of an inflammatory disease, including a lyophilizate of a Taheebo alcohol extract prepared by (a) extracting Taheebo with an alcohol and concentrating an extract; and (b) lyophilizing the alcohol-extracted and concentrated Taheebo.

The lyophilizate of a Taheebo alcohol extract and the extraction process and drying process for preparing the lyophilizate are as described above.

Further, the inflammatory disease may be one or more selected from the group consisting of allergies, dermatitis, atopy, conjunctivitis, periodontitis, rhinitis, otitis media, laryngopharyngitis, tonsillitis, pneumonia, gastric ulcers, gastritis, Crohn's disease, colitis, gout, ankylosing spondylitis, rheumatic fever, lupus, fibromyalgia, psoriatic arthritis, osteoarthritis, rheumatoid arthritis, periarthritis, tendonitis, tenosynovitis, peritendinitis, myositis, hepatitis, cystitis, nephritis, Sjogren's syndrome, multiple sclerosis, and acute and chronic inflammatory diseases.

Specifically, the cosmetic composition includes, but is not limited to, a composition selected from the group consisting of water-soluble vitamins, oil-soluble vitamins, polymer peptides, polymeric polysaccharides, sphingolipids and seaweed extracts.

As the water-soluble vitamin, any substance may be used as long as it may be incorporated in cosmetics, and preferably, vitamin B1, vitamin B2, vitamin B6, pyridoxine, pyridoxine hydrochloride, vitamin B12, pantothenic acid, nicotinic acid, nicotinic acid amide, folic acid, vitamin C, vitamin H and the like may be used, and the salts thereof (thiamine hydrochloride, sodium ascorbate, etc.) or the derivatives thereof (sodium ascorbic acid-2-phosphate, magnesium ascorbic acid-2-phosphate etc.) may be included, but the present invention is not limited thereto.

As the oil-soluble vitamin, any substance may be used as long as it may be incorporated in cosmetics, and preferably, examples thereof include vitamin A, carotene, vitamin D2, vitamin D3, vitamin E (dl-alpha-tocopherol, d-alpha-tocopherol, d-alpha-tocopherol) and the derivatives thereof (ascorbic acid palmitate, ascorbic acid stearate, ascorbic acid dipalmitate, dl-alpha-tocopherol acetate, nicotinic acid dl-alpha-tocopherol vitamin E, DL-pantothenyl alcohol, D-pantothenyl alcohol, pantothenyl ethyl ether, etc.), but the present invention is not limited thereto.

The polymeric peptide may be any substance as long as it may be incorporated in cosmetics, and collagen, hydrolyzed collagen, gelatin, elastin, hydrolyzed elastin or keratin are preferable, but the present invention is not limited thereto.

The polymeric polysaccharide may be any substance as long as it may be incorporated in cosmetics, and is preferably, hydroxyethylcellulose, xanthan gum, sodium hyaluronate, chondroitin sulfate or salts thereof (sodium salt, etc.), but the present invention is not limited thereto.

The sphingo lipid may be any substance as long as it may be incorporated in cosmetics, and ceramides, phytosphingosine and sphingoglycolipids are preferred, but the present invention is not limited thereto.

The seaweed extract may be any substance as long as it may be incorporated in cosmetics, and a brown algae extract, a red algae extract or a green algae extract are preferred, and carrageenan, alginic acid, sodium alginate or potassium alginate purified from the seaweed extract are preferred, but the present invention is not limited thereto.

In addition to the above-mentioned essential components, the cosmetic composition may be mixed with other components commonly added to cosmetics, as necessary. Preferably, examples of the other components include a fat component, a humectant, an emollient, a surfactant, organic and inorganic pigments, an organic powder, a UV absorber, an antiseptic, a bactericide, an antioxidant, an herbal extract, a pH regulating agent, an alcohol, a colorant, an aromatic, a blood flow stimulant, a cooling agent, an antiperspirant or purified water, but the present invention is not limited thereto.

As the fat component, an ester-based fat, a hydrocarbon-based fat, a silicone-based fat, a fluorine-based fat, an animal fat or a vegetable fat is preferred, but the present invention is not limited thereto. Preferably, examples of the ester-based fat include glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, ethyl linoleate, isopropyl linoleate, ethyl oleate, isocetyl myristate, isostearyl myristate, isostearyl palmitate, octyldodecyl myristate, isocertyl isostearate, diethyl sebacate, diisopropyl adipate, isoalkyl neopentanoate, tri(caprylic, capric acid)glyceryl, tri-2-ethylhexanetrimethylolpropane, trimethylolpropane triisostearate, tetra-2-ethylhexanepentaerythritol, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl palmitate, octyl stearate, isocetyl stearate, isodecyl oleate, octyldodecyl oleate, octyldodecyl linolate, isopropyl isostearate, 2-ethylhexanecetostearyl, 2-ethylhexanestearyl, hexyl isostearate, ethylene glycol dioctanate, ethylene glycol dioleate, propylene glycol dicaprylate, di(caprylic, capric acid)propylene glycol, propylene glycol dicaprylate, neopentyl glycol dicaprate, neopentyl glycol dioctanate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglycerineoleic acid ester, polyglycerineisostearic acid ester, triisocetyl citrate, triisoalkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di-2-ethylhexyl succinate, diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate and the like, but the present invention is not limited thereto.

The hydrocarbon-based fat is preferably a hydrocarbon-based oil such as squalene, liquid paraffin, alpha-olefin oligomer, isoparaffin, ceresin, paraffin, floating isoparaffin, polybutene, microcrystalline wax, Vaseline or the like, but the present invention is not limited thereto.

The silicone-based fat is preferably polymethyl silicone, methylphenyl silicone, methyl cyclopolysiloxane, octamethyl polysiloxane, decamethyl polysiloxane, dodecamethylcyclosiloxane, a dimethylsiloxane methyl cetyloxysiloxane copolymer, a dimethylsiloxane methyl stearoxysiloxane copolymer, an alkyl-modified silicone oil or an amino-modified silicone oil, but the present invention is not limited thereto.

The fluorine-based fat is preferably a perfluoropolyether, but the present invention is not limited thereto.

The animal or vegetable fat is preferably avocado oil, almond oil, olive oil, sesame oil, rice bran oil, safflower oil, soybean oil, corn oil, rapeseed oil, apricot oil, palm kernel oil, palm oil, castor oil, sunflower oil, grape seed oil, cottonseed oil, coconut oil, kukui nut oil, wheat germ oil, rice germ oil, shea butter, evening primrose oil, macadamia nut oil, meadowfoam oil, egg yolk oil, tallow, horse oil, mink oil, orange roughy oil, jojoba oil, candelilla wax, carnauba wax, liquid lanolin, hydrogenated castor oil or the like, but the present invention is not limited thereto.

The humectant is preferably a water-soluble low-molecular humectant, a fat-soluble molecular humectant, a water-soluble polymer or a fat-soluble polymer, but the present invention is not limited thereto. The water-soluble low-molecular humectant is preferably serine, glutamine, sorbitol, mannitol, pyrrolidone-sodium carboxylate, glycerine, propylene glycol, 1,3-butylene glycol, ethyleneglycol, polyethyleneglycol B (degree of polymerization (n) of at least 2), polypropylene glycol (degree of polymerization (n) of at least 2), polyglycerine B (degree of polymerization (n) of at least 2), lactic acid or a lactate, but the present invention is not limited thereto. The fat-soluble low-molecular humectant is preferably cholesterol or a cholesterol ester, but the present invention is not limited thereto. The water-soluble polymer is preferably a carboxyvinyl polymer, polyaspartate, tragacanth, xanthan gum, methyl cellulose, hydroxymethyl cellulose, hydroxyethyl cellulose, hydroxypropyl cellulose, carboxymethyl cellulose, water-soluble chitin, chitonic acid or dextrin, but the present invention is not limited thereto. The fat-soluble polymer is preferably a polyvinylpyrrolidone/eicosene copolymer, a polyvinylpyrrolidone/hexadecene copolymer, nitrocellulose, dextrin fatty acid ester or a polymer-silicon, but the present invention is not limited thereto. The emollient is preferably long-chain acyl glutamic acid cholesteryl ester, hydroxystearic acid cholesteryl, 12-hydroxystearic acid, stearic acid, rosin acid, or lanolin fatty acid cholesteryl ester, but the present invention is not limited thereto.

The surfactant is preferably a non-ionic surfactant, an anionic surfactant, a cationic surfactant or an amphoteric surfactant, but the present invention is not limited thereto. The non-ionic surfactant is preferably self-emulsified glycerine monostearate, propylene glycol fatty acid ester, glycerine fatty acid ester, polyglycerine fatty acid ester, sorbitan fatty acid ester, polyoxyethylene (POE) sorbitan fatty acid ester, POE sorbite fatty acid ester, POE glycerine fatty acid ester, POE alkylether, POE fatty acid ester, POE hydrogenated castor oil, POE castor oil, a POE/polyoxypropylene (POP) copolymer, POE/POP alkylether, polyether-modified silicon, lauric acid alkanol amide, an alkylamine oxide or a hydrogenated soybean phospholipid, but the present invention is not limited thereto. The anionic surfactant is preferably fatty acid soap, an α-acylsulfonate, an alkylsulfonate, an alkylarylsulfonate, an alkylnaphthalenesulfonate, an alkylsulfate, a POE alkylethersulfate, an alkylamidesulfate, an alkylphosphate, a POE alkylphosphate, an alkylamidephosphate, an alkyloylalkyltaurate, N-acylamino acid salt, a POE an alkylethercarboxylate, an alkylsulfosuccinate, a sodium alkylsulfoacetate, an acylated hydrolyzed collagen peptide salt or a perfluoroalkyl phosphate ester, but the present invention is not limited thereto. The cationic surfactant is preferably an alkyltrimethyl ammonium chloride, stearyltrimethyl ammonium chloride, stearyltrimethyl ammonium bromide, cetostearyltrimethyl ammonium chloride, distearyldimethyl ammonium chloride, stearyldimethylbenzyl ammonium chloride, behenyltrimethyl ammonium bromide, benzalkonium chloride, diethylaminoethylamide stearate, dim ethylaminopropylamide stearate or quaternary ammonium derivatives of lanolin, but the present invention is not limited thereto. The amphoteric surfactant is preferably a carboxybetaine-type, amide betaine-type, sulfobetaine-type, hydroxyl sulfobetaine-type, amide sulfobetaine-type, phosphobetaine-type, aminocarboxylate-type, imidazoline derivative-type or amideamine-type amphoteric surfactant, but the present invention is not limited thereto.

Preferably, examples of the organic and inorganic pigment include an inorganic pigment such as silicic acid, silicic acid anhydride, magnesium silicate, talc, sericite, mica, kaolin, bengala, clay, bentonite, titan-coated mica, bismuth oxychloride, zirconium oxide, magnesium oxide, zinc oxide, titanium oxide, aluminium oxide, calcium sulfate, barium sulfate, magnesium sulfate, calcium carbonate, magnesium carbonate, iron oxide, ultramarine, chromium oxide, chromium hydroxide, calamine and a complex thereof; an organic pigment such as polyamide, polyester, polypropylene, polystyrene, polyurethane, a vinyl resin, a urea resin, a phenol resin, a fluorine resin, a silica resin, an acrylic resin, a melamine resin, an epoxy resin, a polycarbonate resin, a divinylbenzene/styrene copolymer, silk powder, cellulose, a CI Pigment Yellow, or a CI Pigment Orange; and a complex pigment of the inorganic pigment and the organic pigment, but the present invention is not limited thereto.

Preferably, examples of the organic powder include a metallic soap such as calcium stearate; a metal alkylphosphate such as zinc sodium cetylate, zinc laurylate or calcium laurylate; a polyvalent acylamino acid metal salt such as N-lauroyl-β-alanine calcium, N-lauroyl-β-alanine zinc or N-lauroyl glycine calcium; a polyvalent amide sulfonic acid metal salt such as N-lauroyl-taurine calcium or N-palmitoyl-taurine calcium; a N-acyl basic amino acid such as N-ε-lauroyl-L-lysine, N-ε-palmitoyllysine, N-α-palmitoyl ornithine, N-α-lauroylarginine, or N-α-hydrogenated tallow fatty acid acyl arginine; an N-acylpolypeptide such as N-lauroylglycylglycine; an α-amino fatty acid such as α-amino caprylic acid, or α-amino lauric acid; polyethylene, polypropylene, nylon, polymethylmethacrylate, polystyrene, a divinylbenzene/styrene copolymer or tetrafluoroethylene, but the present invention is not limited thereto.

Preferably, examples of the UV absorber include para-amino benzoic acid, ethyl-para-aminobenzoate, amyl-para-aminobenzoate, octyl-para-aminobenzoate, ethylene glycol salicylate, phenyl salicylate, octyl salicylate, benzyl salicylate, butylphenyl salicylate, homomentyl salicylate, benzyl cinnamate, 2-ethoxyethyl para-methoxy cinnamate, octyl para-methoxy cinnamate, mono-2-ethyl hexane glyceryl di-para-methoxy cinnamate, isopropyl para-methoxy cinnamate, a diisopropyl/diisopropyl cinnamic acid ester mixture, urocanic acid, ethyl urocanate, hydroxy methoxybenzophenone, hydroxyl methoxybenzophenone sulfonic acid and salts thereof, dihydroxy methoxybenzophenone, sodium dihydroxy methoxybenzophenone disulfonate, dihydroxy benzophenone, tetrahydroxy benzophenone, 4-tert-butyl-4'-methoxy dibenzoylmethane, 2,4,6-trianilino-p-(carbo-2'-ethylhexyl-1'-oxy)-1,3,5-triazine or 2-(2-hydroxy-5-methyl-phenyl)benzotriazole, but the present invention is not limited thereto.

Preferably, examples of the bactericide include hinokitiol, triclosan, trichlorohydroxydiphenyl ether, chlorhexidine gluconate, phenoxy ethanol, resorcin, isopropylmethylphenol, azulene, salicylic acid, zinc pyrithione, benzalkonium chloride, photosensitizer 301, sodium mononitroguaiacol or undecylenic acid, but the present invention is not limited thereto.

Preferably, examples of the antioxidant include butylhydroxy anisole, propyl gallate or erythorbic acid, but the present invention is not limited thereto.

Preferably, examples of the pH regulating agent include citric acid, sodium citrate, malic acid, sodium malate, fumaric acid, sodium fumarate, succinic acid, sodium succinate, sodium hydroxide or disodium hydrogen phosphate, but the present invention is not limited thereto.

The alcohol is preferably a higher alcohol such as cetyl alcohol, but the present invention is not limited thereto.

In addition, a mixing component which may be added herein is not limited to the above-described components, and any component may be mixed in such a range that the objects and effects of the present invention are not hindered. The component may be preferably mixed in an amount of 0.01 to 5 wt %, and more preferably in an amount of 0.01 to 3 wt %, based on the total weight, but the present invention is not limited thereto.

The cosmetic composition may be prepared in the form of a solution, an emulsion or a viscous mixture, but the present invention is not limited thereto.

In addition to the compounds, the components included in the cosmetic composition may further include components generally used for a cosmetic composition as active ingredients, and may include a conventional adjuvant and carrier such as a stabilizing agent, a solubilizing agent, a vitamin, a pigment and an aromatic, but the present invention is not limited thereto.

The cosmetic composition may be prepared into any formulation which is generally prepared in the related field, and may be prepared into a milky lotion, a cream, a facial lotion, a pack, a foundation lotion, a lotion, an essence or a hair care composition, but the present invention is not limited thereto. Specifically, the cosmetic composition includes formulations of skin lotions, skin softeners, skin toners, astringents, lotions, milk lotions, moisturizing lotions, nutrient lotions, massage creams, nutrient creams, moisturizing creams, hand creams, foundations, essences, nutrient essences, packs, cleansing foams, cleansing lotions, cleansing creams, body lotions or body cleansers, but the present invention is not limited thereto.

When the formulation is in the form of a paste, cream or gel, an animal fiber, a vegetable fiber, a wax, paraffin, a starch, tragacanth, a cellulose derivative, polyethylene glycol, silicon, bentonite, silica, talc or zinc oxide may be used as a carrier component, but the present invention is not limited thereto.

When the formulation is in the form of a powder or spray, lactose, talc, silica, aluminum hydroxide, calcium silicate or polyamide powder may be used as the carrier component. Particularly, when the formulation is in the form of spray, the formulation may further include a propellant such as chlorofluorohydrocarbon, propane/butane or dimethylether, but the present invention is not limited thereto.

When the formulation is in the form of a solution or emulsion, a solvent, a solvating agent or an emulsifying agent may be used as the carrier component, and water, ethanol, isopropanol, ethyl carbonate, ethyl acetate, benzyl alcohol, benzyl benzoate, propylene glycol, 1,3-butylglycol oil, aliphatic glycerol ester, polyethylene glycol, or sorbitan fatty acid ester may be used, but the present invention is not limited thereto.

When the formulation is in the form of a suspension, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum methahydroxide, bentonite, agar or tragacanth may be used as the carrier component, but the present invention is not limited thereto.

When the formulation is in the form of surfactant-containing cleanser, an aliphatic alcohol sulfate, an aliphatic alcohol ether sulfate, sulfosuccinic acid monoester, isethionate, an imidazolium derivative, methyltaurate, sarcosinate, fatty acid amide ether sulfate, alkylamido betaine, an aliphatic alcohol, fatty acid glyceride, fatty acid diethanolamide, a vegetable oil, a lanolin derivative or ethoxylated glycerol fatty acid ester may be used as the carrier component, but the present invention is not limited thereto.

According to another embodiment of the present invention, the present invention provides a method of treating an inflammatory disease including administering the composition to a subject.

In the present invention, the term "subject" refers to a subject having a disease to be treated, and more specifically, mammals such as humans or non-human primates, mice, rats, dogs, cats, horses, cattle, etc.

Further, the present invention provides a prophylactic or therapeutic use of an inflammatory disease including the composition.

Hereinafter, exemplary examples of the invention will be described for promoting an understanding of the invention. However, the following examples should be considered in a descriptive sense only and the scope of the invention is not limited to the following examples.

EXAMPLES

Example 1

An inner bark portion of Brazilian Taheebo (Tabebuia Avellanedae) was purchased. The inner bark portion was mixed with 10 (v/w) times as much of a 50 (v/v)% alcohol, and then a mixture was extracted using a reflux extraction method at 55° C. for 4 hours. Then, the mixture was filtered under reduced pressure and concentrated using a rotary vacuum concentrator. Thereafter, the mixture was lyophilized at −40° C. for 72 hours to prepare a lyophilizate of a 50 (v/v)% alcohol extract of Taheebo.

Example 2

A lyophilizate of a 70 (v/v)% alcohol extract of Taheebo was prepared in the same manner as in Example 1 except that a 50 (v/v)% alcohol was changed to a 70 (v/v)% alcohol.

Example 3

A lyophilizate of a 90 (v/v)% alcohol extract of Taheebo was prepared in the same manner as in Example 1 except that a 50 (v/v)% alcohol was changed to a 90 (v/v)% alcohol.

Example 4

A lyophilizate of a 80 (v/v)% alcohol extract of Taheebo was prepared in the same manner as in Example 1 except that a 50 (v/v)% alcohol was changed to a 80 (v/v)% alcohol.

The indicator components of the lyophilizate of a 80 (v/v)% alcohol extract of Taheebo were analyzed by HPLC.

Specifically, 200 mg of veratric acid was precisely weighed, placed in a 200-mL volumetric flask, methanol was filled up to a gauge mark, and ultrasonic treatment was performed to dissolve a mixture to prepare a standard stock solution. Further, the standard stock solution was diluted with methanol to a concentration of 33% (50 µg/mL) to 333% (500 µg/mL) with respect to the reference concentration of veratric acid (about 150 µg/mL, 100%) to prepare a standard solution as follows.

TABLE 1

| Veratric acid (µg/mL) | 50 | 100 | 150 | 300 | 500 |
|---|---|---|---|---|---|
| % Relative to reference concentration | 33% | 67% | 100% | 200% | 333% |

Next, 100 mg of the lyophilizate of a 80 (v/v)% alcohol extract of Taheebo was precisely weighed and placed in a 10 mL flask. About 9 mL of methanol was added thereto, and a mixture was ultrasonicated for 15 minutes. The mixture was allowed to stand at room temperature for 30 minutes so that the temperature of a solvent was lowered to room temperature. Then, methanol was added up to a 10 mL mark, and the mixture was sufficiently mixed by vortexing to prepare a test solution. Thereafter, the test solution was transferred to a 15 mL conical tube and centrifuged to submerge a methanol insoluble residue in a sample. Then, 1 mL of a supernatant was taken with an auto-pipet and filtered with a 0.45 µm membrane filter, and analyzed by HPLC. The area of the peak of veratric acid was measured.

Content (µg/g) of veratric acid in lyophilizate of 80(v/v)% alcohol extract of Taheebo=$(A \times B)/C$ A: Total amount of test solution (mL) (=10 mL) B: Concentration (µg/mL) of veratric acid of test solution calculated from calibration curve C: Amount (g) of collected lyophilizate of 80(v/v)% alcohol extract of Taheebo As a result of analysis, it is confirmed that the content of veratric acid in the lyophilizate of an 80(v/v)% alcohol extract of Taheebo was about 1.588(w/w)% (15.58 mg/g).

Comparative Example 1

A lyophilizate of a hot water extract of Taheebo was prepared in the same manner as in Example 1 except that, instead of alcohol extraction, the inner bark portion was mixed with 10 (v/w) times as much distilled water, and the mixture was refluxed and extracted at 95° C. for 3 hours.

Comparative Example 2

A lyophilizate of a 30 (v/v)% alcohol extract of Taheebo was prepared in the same manner as in Example 1 except that a 50 (v/v)% alcohol was changed to a 30 (v/v)% alcohol.

Comparative Example 3

A spraying dry matter of hot water extract of Taheebo was prepared in the same manner as in Comparative Example 1 except that, instead of lyophilization, 50 wt % of dextrin was mixed based on the total weight of hot water-extracted and concentrated Taheebo to perform spray-drying.

Comparative Example 4

A spraying dry matter of a 30 (v/v)% alcohol extract of Taheebo was prepared in the same manner as in Comparative Example 3 except that, instead of hot water extraction, the inner bark portion was mixed with 10 (v/w) times as much of a 30 (v/v)% alcohol, and reflexed and extracted at 55° C. or 4 hours.

Comparative Example 5

A spraying dry matter of a 50 (v/v)% alcohol extract of Taheebo was prepared in the same manner as in Comparative Example 4 except that a 30 (v/v)% alcohol was changed to a 50 (v/v)% alcohol.

Comparative Example 6

A spraying dry matter of a 70 (v/v)% alcohol extract of Taheebo was prepared in the same manner as in Comparative Example 4 except that a 30 (v/v)% alcohol was changed to a 70 (v/v)% alcohol.

Comparative Example 7

A spraying dry matter of a 90 (v/v)% alcohol extract of Taheebo was prepared in the same manner as in Comparative Example 4 except that a 30 (v/v)% alcohol was changed to a 90 (v/v)% alcohol.

TABLE 2

| | Extraction process | Drying process |
|---|---|---|
| Example 1 | 50(v/v)% alcohol | Lyophilization |
| Example 2 | 70(v/v)% alcohol | |
| Example 3 | 90(v/v)% alcohol | |
| Comparative Example 1 | Hot water | |
| Comparative Example 2 | 30(v/v)% alcohol | |
| Comparative Example 3 | Hot water | Spray-drying |
| Comparative Example 4 | 30(v/v)% alcohol | |
| Comparative Example 5 | 50(v/v)% alcohol | |
| Comparative Example 6 | 70(v/v)% alcohol | |
| Comparative Example 7 | 90(v/v)% alcohol | |

Experimental Example 1

Determination of Inhibitory Effect of Nitric Oxide Synthesis

In order to compare the inhibitory effect of nitric oxide synthesis of the lyophilizates of the 50 to 90 (v/v)% alcohol extracts of Taheebo prepared in Examples 1 to 3 with the lyophilizates of the extracts of Taheebo according to Comparative Examples 1 to 7, RAW264.7 cells, which is a murine macrophage cell line, were cultured in a 100 mm cell culture dish using an RPMI 1640 medium containing penicillin (100 IU/ml), streptomycin (100 µg/ml) and 10%-FBS to a density of 70 to 80%.

After RAW264.7 cells, which is a murine macrophage cell line, were adjusted to have a concentration of $1 \times 10^6$ cell/ml using the RPMI 1640 medium containing penicillin (100 IU/ml), streptomycin (100 µg/ml) and 10%-FBS, the cells were inoculated in a 96-well plate, and precultured at 5% $CO_2$ and 37° C. for 18 hours. Then, the medium was removed, 50 μl of the extract prepared at a concentration of 4 times was pretreated for 30 minutes, and then cultured in a medium containing 50 μl of LPS (a final concentration of 1 μg/ml). After 24 hours, the supernatant was transferred to another 96-well plate in an amount of 100 μl. The quantification of nitric oxide (NO) was performed by measuring an absorbance at 540 nm using a Griess solution (0.5% naphthylethyleneamine dihydrochloride, 5% sulfanilamide and 25% $H_3PO_4$). Calibration curves were prepared using sodium nitrite (0 to 100 μM) as a standard material.

Figure 2:
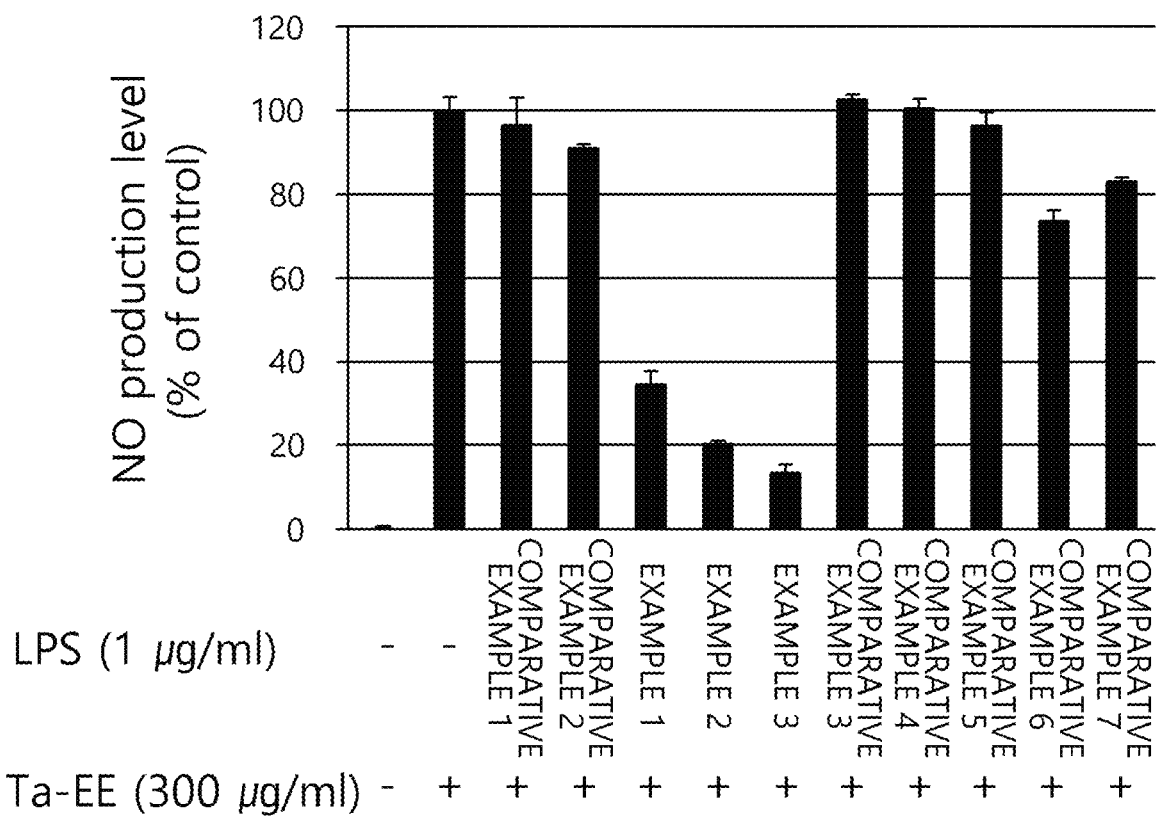
FIG. 2 is a graph comparing the inhibitory effect of nitric oxide synthesis of the lyophilizate of a 50 to 90 (v/v)% alcohol extract of Taheebo prepared in Examples 1 to 3 and dry extract matter of Taheebo according to Comparative Examples 1 to 7.

FIG. 2 is a graph comparing the inhibitory effect of nitric oxide synthesis of the lyophilizates of the 50 to 90 (v/v)% alcohol extracts of Taheebo prepared in Examples 1 to 3 with the lyophilizates of the extracts of Taheebo according to Comparative Examples 1 to 7.

As shown in FIG. 2, the lyophilizates of the 50 to 90(v/v)% alcohol extracts of Taheebo prepared in Examples 1 to 3 has a nitric oxide synthesis level of less than 40% as compared with control groups, and thus it can be confirmed that the inhibitory effect of nitric oxide synthesis is significantly superior to that of the lyophilizates of the extracts of Taheebo according to Comparative Examples 1 to 7.

The foregoing description of the present invention has been presented for the purposes of illustration and description. It is apparent to a person having ordinary skill in the art to which the present invention relates that the present invention can be easily modified into other detailed forms without changing the technical principle or essential features of the present invention. Therefore, the foregoing embodiments should be regarded as illustrative rather than limiting in all aspects. For example, each component which has been described as a single part can be implemented as distributed parts. Likewise, each component which has been described as distributed parts can also be implemented as a combined part.

The invention claimed is:

1. A method of preparing an anti-inflammatory Taheebo extract comprising veratric acid, said method comprising:
    (a) extracting Taheebo with an alcohol comprising ethanol in a range of 70 to 90 (v/v) %; and
    (b) lyophilizing said alcohol extract solution to produce said anti-inflammatory Taheebo extract comprising a therapeutically effective amount of veratric acid.

2. The method of claim 1, wherein, in Step (a), the extracting is performed at a temperature of 40 to 80° C. for 3 to 10 hours.

3. The method of claim 1, wherein said step of lyophilizing is performed at a temperature of −30 to −50° C. for 48 to 168 hours.

4. The method of claim 1, wherein the lyophilizate of a Taheebo alcohol extract has an inhibitory effect of nitric oxide synthesis.

* * * * *